(12) United States Patent
Arnold et al.

(10) Patent No.: US 12,247,970 B2
(45) Date of Patent: Mar. 11, 2025

(54) METHOD FOR THE ASSESSMENT OF ALKALI-SILICA REACTIVITY OF AGGREGATES AND CONCRETE MIXTURES

(71) Applicants: Terence S Arnold, Washington Grove, MD (US); Chandni Balachandran, McLean, VA (US); Jose F Munoz, Ellicott City, MD (US)

(72) Inventors: Terence S Arnold, Washington Grove, MD (US); Chandni Balachandran, McLean, VA (US); Jose F Munoz, Ellicott City, MD (US)

(73) Assignee: The U.S. Department of Transportation. Federal Highway Administration, Washington, DC (US)

( * ) Notice: Subject to any disclaimer, the term of this patent is extended or adjusted under 35 U.S.C. 154(b) by 553 days.

(21) Appl. No.: 17/112,090

(22) Filed: Dec. 4, 2020

(65) Prior Publication Data

US 2022/0317109 A1 Oct. 6, 2022

(51) Int. Cl.
*G01N 33/38* (2006.01)
*C04B 40/00* (2006.01)

(52) U.S. Cl.
CPC ....... *G01N 33/383* (2013.01); *C04B 40/0032* (2013.01); *C04B 40/0082* (2013.01)

(58) Field of Classification Search
CPC ...... G01N 33/20; G01N 33/38; G01N 33/383; C04B 40/0032; C04B 40/0082;
(Continued)

(56) References Cited

U.S. PATENT DOCUMENTS 5,739,035 A * 4/1998 Guthrie, Jr. .......... G01N 33/383
436/72
2016/0209372 A1* 7/2016 Ziehl ..................... G01N 29/46
2021/0319377 A1* 10/2021 Dittrich .................. G01N 21/65

FOREIGN PATENT DOCUMENTS

JP 2005291944 A * 10/2005
JP 3138018 B2 * 2/2011
JP 6628362 B2 * 12/2019

OTHER PUBLICATIONS

Munoz et al. "New Chemical Reactivity Index to Assess Alkali-Silica Reactivity", Jour. Mater. Civ. Eng., vol. 33(4), 2021, pp. 04021037-1-04021037-15.*

* cited by examiner

*Primary Examiner* — Maureen Wallenhorst
(74) *Attorney, Agent, or Firm* — Charles R Ducker, Jr.

(57) ABSTRACT

Chemical test methods for evaluating the alkali-silica reactivity (ASR) of an aggregate or an aggregate within a particular concrete job mix design by exposing the aggregate to a simplified system with the same or simulated long-term pore solution conditions is provided. ASR is a chemical reaction occurring between alkaline hydroxides within cement paste and certain types of amorphous silica found in mineral aggregates. Causing an accumulation of internal pressure within concrete structures due to the formation of a hygroscopic gel through the absorption of water, ASR leads to expansion and cracking of concrete. The present test method determines the reactivity index (RI) of a given aggregate, or an aggregate as it is to be used in a proposed concrete job mix design by determining the average concentrations of calcium, aluminum, and silicon across multiple tested samples, wherein the RI is the ratio of the concentrations of silicon to that of aluminum and calcium combined.

19 Claims, 1 Drawing Sheet

(58) Field of Classification Search
CPC .......... C04B 2111/2023; Y10T 436/25; Y10T 436/25375; Y10T 436/255
USPC ............. 436/72, 73, 79, 147, 174, 177, 178
See application file for complete search history.

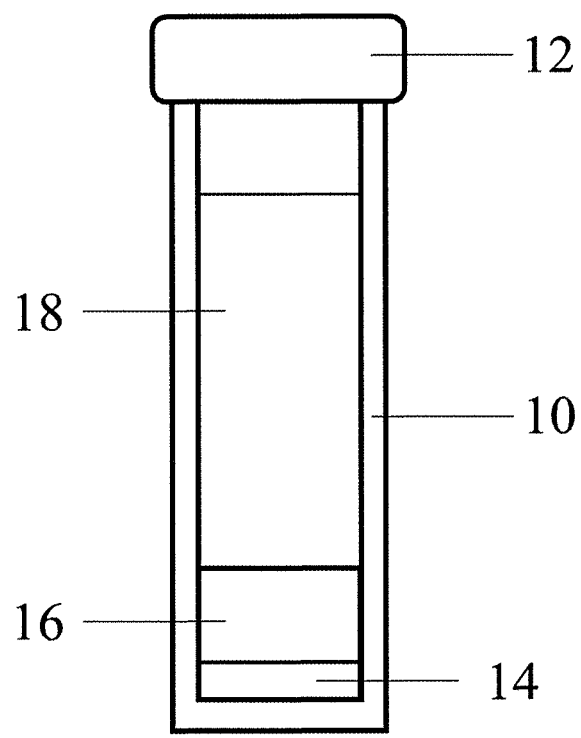

METHOD FOR THE ASSESSMENT OF ALKALI-SILICA REACTIVITY OF AGGREGATES AND CONCRETE MIXTURES

STATEMENT REGARDING FEDERALLY SPONSORED RESEARCH OR DEVELOPMENT

This invention was made with government support provided by the Federal Highway Administration, an Operating Administration of the U.S. Department of Transportation. The government has certain rights in the invention.

FIELD OF THE DISCLOSURE

The invention generally relates to chemical testing methods for determining alkali-silica reactivity. More particularly, the present invention relates to a method for assessing the likelihood of the formation of expansive alkali-silica gels in concrete over time. The invention provides a test method useful for assessing the alkali-silica reactivity susceptibility of either a fine or coarse aggregate, as well as for assessing the alkali-silica reactivity susceptibility of a mixed aggregate in a particular concrete job mix. The test method determines alkali-silica reactivity susceptibility by exposing an aggregate or a mixed aggregate in a particular job mix design to the same long-term pore solution conditions in which it will be used.

BACKGROUND OF THE DISCLOSURE

Concrete is widely used around the world for the construction of infrastructure, including highways, bridges, residential and commercial buildings, dams, electric power generation plants, and nuclear power plants. The heterogeneous nature of concrete makes it susceptible to various deterioration mechanisms including corrosion of reinforcement, sulfate attack, alkali-silica reaction (ASR), freeze-thaw cycling, leaching, radiation, elevated temperatures, salt crystallization, and microbiological attack. Concrete deterioration may jeopardize the serviceability and safety of structures leading to economic losses and ultimately to catastrophic failures and fatalities. It is, therefore, necessary to evaluate the materials used to make the concrete used in such structures to protect and extend their effective service life.

The discovery of cracks from alkali-silica reaction (ASR) in the concrete of numerous concrete highway structures in California in the 1940s brought this type of deterioration of concrete to the attention of the general public and established a need for a method for determining the likelihood of the occurrence of this destructive process. In the formation of ASR gels, the chemical reaction between the siliceous phases present in some aggregates and the hydroxyl ions in the pore solution of the concrete form an alkali-silica gel. The mechanism requires as little as 80-percent relative humidity to occur. The reaction product is an amorphous material that swells when moisture is absorbed and can cause expansion and cracking in concrete structures.

Despite having been known since the 1940s, there is no efficient, accurate, and accelerated test method to evaluate the alkali-silica reactivity of aggregates. The American Society for Testing and Materials standards ASTM C1260 and ASTM C1293 are presently the most popular alternative testing methodologies for local and state Departments of Transportation to minimize the risk of ASR development in concrete infrastructure. The standards ASTM C 1778-16 and AASHTO R 80-17 propose an overall management plan, including the identification and implementation of prevention measures, based on petrographic analysis (ASTM C295 and C856) and accelerated methods of mortar (ASTM C1260 and C1567) and concrete (ASTM C1293) analysis. This holistic approach, however, has important drawbacks mainly motivated by the complexity of the proposed decision chart to evaluate a source of aggregate for potential ASR. This complexity makes the evaluation process highly inefficient due to the cost and extent of the process.

As noted above, the ASTM C1260 and C1293 test methodologies are presently the most popular guidelines and test methods. In addition, there are additional testing methods for evaluating the potential of aggregates for ASR reactivity. The ASTM C295 standard guide is used to determine the physical and mineralogical characteristics of aggregates. Typically, this petrographic examination requires the use of optical microscopy to classify different rock types and mineral constituents within an aggregate. Identifying constituents of an aggregate is generally a necessary step in determining the properties that may be expected to influence behavior, such as ASR subjectivity, during intended use. Because potentially deleterious minerals such as reactive silica present in an aggregate can be identified using petrographic examination it is may be used as a criterion in the proper selection of materials to prevent ASR. However, petrography is limited in that certain types of slowly-reactive minerals such as microcrystalline, strained, or microfractured quartz cannot be clearly identified and these minerals are commonly occurring in a wide variety of aggregates. Another drawback to the C295 test method is that the interpretation of results can vary widely depending on the petrographer's experience level and background.

The ASTM C1260 is a test method which permits the detection within 16 days of the potential of an aggregate in mortar bars to develop deleterious ASR expansion. The ASR reaction is accelerated by exposing mortar bars to a 1 N sodium hydroxide solution which is kept at 80° C. The alkaline soaking solution provides the mortar bar with essentially an unlimited supply of hydroxides in order to accelerate the reaction. This test is considerably valuable because it provides a rapid means of evaluating potentially reactive aggregates for use in concrete. However, this test method has been reported by many researchers as very severe and it has been shown in the past to identify aggregates as reactive that have good long-term service records. In addition, there are also reported cases of certain aggregates, such as granitic-gneiss, metadacite, or granodiorite, that have passed the test, but which have exhibited ASR distress in the field.

The ASTM C1293 is a test method used to determine, through the measurement of length change of concrete prisms, the susceptibility of a sample aggregate for participation in expansive ASR. Commonly referred to as the "Concrete Prism Test", this test method was developed to more accurately identify aggregates subject to ASR. Much like ASTM C1260, the ASTM C1293 test method does not duplicate field conditions and as such actual field behavior of aggregates subject to ASR may not be well represented. It is, therefore, important that the ASTM C1293 be used as a criterion, in conjunction with other practices, to evaluate reactivity of aggregates. Nevertheless, the ASTM C1293 test method has been shown to provide the best correlation with actual field performance among known test methods and is currently regarded as the most authoritative test for evaluating aggregates for ASR. This test method, however, suffers from limitations, including its long test period, significant leaching of alkalis from the specimen during the test, and unsuitability for the evaluation of a specific job mix design.

Additionally, there are many standards guides and test methods that have been withdrawn. The ASTM C289, for example, was a test method covering the chemical determination of the potentially reactivity of an aggregate. A substantial number of well-known ASR reactive aggregates were shown to pass this test, while many innocuous aggregates were identified as deleterious. Additionally, the interference of certain elements, such as calcium and magnesium, as well as minerals, such as silicates, gypsum, zeolites, clay minerals, organic matter, and iron oxides, were shown to cause erroneous results. As a result, this test method was withdrawn in 2016. The ASTM C227 test method was used to determine the susceptibility of cement-aggregate combinations to expansive alkali-aggregate reactions, including ASR, but was determined to suffer from severe alkali leaching and false negatives with slow reactive aggregates. It was withdrawn in 2018.

The limitations associated with the above laboratory tests clearly show the need for an improved, all-encompassing method for predicting ASR reactivity of aggregates and of aggregates in a proposed concrete job mix design. State departments of transportation and the construction industry are desirous for an accurate, rapid, and reliable test method capable of mimicking the composition of the pore solution in the concrete at the time of initiation of ASR, evaluate proposed job mixes using a specified aggregate, and mirror the field performance of concrete.

SUMMARY OF THE DISCLOSURE

Objects and advantages of this disclosure will be set forth in part in the following description, or may be learned through practice of the invention.

A method is provided that includes an accelerated chemical test to evaluate the ASR reactivity of an aggregate. The test is flexible and reliable, such that it may be used to evaluate either fine or coarse aggregate, as well as an aggregate for use in a specific concrete job mix design. The test is designed to mimic the long-term pore solution conditions that the aggregate will face in the concrete and results in an ASR reactivity index (RI) number that may be used to classify the aggregate's potential for ASR reactivity. The test measures the concentrations of silicon, aluminum, and calcium in test filtrates after a predefined test period and provides a chart for evaluating the reactivity category of an aggregate based on the calculated RI.

In one embodiment of the present disclosure, the test assesses the ASR reactivity of an aggregate. ASR reactivity is determined by exposing the aggregate to a simplified system with a plurality of pore solution conditions under simulated exposures. The test provides for at least four test conditions with predefined variations in the composition of the simulated pore solution. Three of the test conditions may be used to detect fast reacting aggregates and those that react over a medium length of time. The fourth test condition may be used to detect very slow aggregate reactivity. To more accurately assess the reactivity of the aggregate under each of the at least four test conditions, a plurality of replicates may be prepared for each test condition. The calculated reactivity of the plurality of replicates for each test condition may be averaged to more accurately determine the reactivity of the aggregate under that specific test condition.

In preparing the test for a coarse aggregate, an amount of aggregate may be crushed and divided into two fractions: a finer fraction retained in a #100 sieve and a coarser fraction retained by a #50 sieve. The crushed aggregate may be washed with deionized water and dried fully. A predefined amount of the two fractions of aggregate may be homogenized at a predetermined ratio of finer to coarser fractions of crushed aggregate. For testing of a fine aggregate, the crushing and sifting requirements above are not necessary.

Each replicate may comprise a test tube or other acceptable container comprised of a non-reactive material. The plurality of replicates for each test condition may be prepared by adding a predefined amount of calcium oxide (CaO) to each replicate. The amount of CaO varies for each of the test conditions. Each replicate may then receive at least 5 grams of the aggregate to be tested. For testing of a coarse aggregate, this will be the crushed, shifted, and homogenized aggregate. For testing of a fine aggregate, this will simply be the fine aggregate in the gradation as received. Finally, a predefined amount of a soluble alkali, such as sodium hydroxide (NaOH), or a potassium hydroxide (KOH) may be added to each replicate. Each replicate is then securely sealed.

The plurality of replicates representing the three test conditions used to detect fast reacting aggregates and aggregates that react over a medium length of time may then be placed in a first oven at an elevated temperature for a predefined time. The plurality of replicates representing the fourth test condition and which are used to detect slow reacting aggregates may be placed in a second oven at an elevated temperature higher than that of the first oven for the same predefined time. After the predefined time, the contents of each replicate may be thoroughly mixed and individually vacuum filtered. The filtrate from each replicate may then be individually analyzed for its concentrations of calcium, aluminum, and silicon. The reactivity index (RI) for each replicate may then be calculated by determining the ratio of silicon to that of aluminum and calcium combined.

Using multiple replicates for each of the test conditions allows a tester to average the calculated RI for an aggregate in each of the test conditions. The test provides for characterizing the reactivity of a tested aggregate, by comparing the calculated RI averages for all the test conditions to a chart that indicates the overall reactivity of the aggregate as falling into one of five categories: non-reactive, slow reactive, moderately reactive, highly reactive, and very highly reactive.

In an alternative embodiment of the present disclosure, an accelerated chemical test method is provided for assessing the ASR reactivity of a mixed aggregate in a proposed concrete job mix design. ASR reactivity is determined by exposing the aggregate mix to the long-term pore solution conditions as established by the job mix design and the cement mill report.

In preparing the test, an amount of the coarser portions of the aggregate may be crushed and divided into two fractions: a finer fraction retained in a #100 sieve and a coarser fraction retained by a #50 sieve. These fractions along with the finer aggregate may be mixed at a ratio as declared in the proposed job mix design. A predefined amount of the mixed aggregate may then be homogenized for use in each replicate.

Each replicate may comprise a test tube or other acceptable container comprised of a non-reactive material. A plurality of replicates, each having the same long-term pore conditions as set forth in the job mix design and as established in the cement mill report may be prepared. In this alternative embodiment, the amount of CaO and soluble alkali are not defined by the test methodology. Instead, the composition of the pore solution inside the plurality of replicates—the alkalinity and amount of calcium oxide—are calculated based on the alkali content and the specific amount of portlandite in the proposed concrete job mix design to expose the prepared mixed aggregate to the same long-term pore conditions that it would experience during its proposed use.

Once the amount and concentration of alkali are calculated, the test configuration may be the same as the previous embodiment—at least three replicates may be prepared in non-reactive, sealable containers, in which first the calculated amount of CaO is inserted into each replicate, followed by at least five grams of the prepared mixed of the crushed, shifted, and homogenized coarse aggregate and the calculated amount of fine aggregate, a soluble alkali, such as sodium hydroxide (NaOH) or potassium hydroxide (KOH) required to ensure the proper concentration of alkalis within each replicate. The at least three replicates may then be placed in an oven at a predefined elevated temperature for a set period.

After the set period, the contents of each replicate may be thoroughly mixed and individually vacuum filtered. The filtrate from each replicate may then be individually analyzed for its concentrations of calcium, aluminum, and silicon. The reactivity index (RI) for each replicate may be calculated using the ratio of silicon to that of aluminum and calcium combined.

Using multiple replicates allows a tester to average the calculated RI for the mixed aggregate in the precise long-term pore conditions as proposed in the job mix design. The test provides for characterizing the reactivity of the tested mixed aggregate, by comparing the calculated RI average to a chart that indicates the overall reactivity of the mixed aggregate.

Additional advantages of the disclosure are set forth in, or will be apparent to those of ordinary skill in the art from, the detailed description as follows. It should also be appreciated that modifications and variations to the specifically illustrated and discussed method steps and materials hereof may be practiced in various embodiments and uses of this disclosure without departing from the spirit and scope thereof. Such variations may include, but are not limited to, substitutions of equivalent means, features, and materials for those shown or discussed, and the functional or positional reversal of various parts, features or the like, as well as the reorganization of certain method steps.

Still further, it is to be understood that different embodiments of this disclosure may include various combinations or configurations of presently disclosed features, elements, or their equivalents (including combinations of features or configurations not expressly shown in the figures or stated in the detailed description).

These and other aspects and advantages of the present disclosure will become better understood with reference to the following descriptions and appended claims. The accompanying drawings, which are incorporated in and constitute a part of this specification, illustrate at least one embodiment and, together with the descriptions, serve to explain the principles of this disclosure.

BRIEF DESCRIPTION OF THE DRAWINGS

A full and enabling disclosure, directed to one of ordinary skill in the art, is set forth more particularly in the remainder of the specification, which makes reference to the appended figure, in which:

FIG. 1 is a perspective, cross-section view of an exemplary test replicate including the three components of a test—a predefined amount of aggregate to be tested, a predefined or calculated amount of CaO, and a predefined or calculated amount of an aqueous solution of alkalis.

Repeated use of reference characters throughout the present specification and appended drawing is intended to represent the same or analogous features or elements of the present disclosure.

DETAILED DESCRIPTION

Reference will now be made in detail to the presently preferred embodiment or embodiments of the disclosure, examples of which are fully represented in the accompanying drawings. Such examples are provided by way of an explanation of the disclosure, not a limitation thereof. It should be apparent to those of ordinary skill in the art that various modifications and variations can be made to the presently disclosed embodiments without departing from the spirit and scope thereof. For instance, features illustrated or described as part of one embodiment may be used on another embodiment to yield a further embodiment. Still further, variations in selection of materials and/or characteristics may be practiced and changes to the basic order of method steps, where appropriate may be made to satisfy particular desired user criteria. Thus, it is intended that the present disclosure cover such modifications and variations as come within the scope of the appended claims and their equivalents. It is to be understood by one of ordinary skill in the art that the present disclosure is a description of exemplary embodiments only, and is not intended as limiting the broader aspects thereof.

Alkali-silica reaction (ASR) is one of the primary chemical reactions causing degradation and loss of service of hardened concrete structures worldwide. ASR is a reaction that occurs over time in concrete between aqueous alkaline hydroxides, within the pore solution of the cement paste, and amorphous silica, within surrounding aggregates. The accumulation of expansive pressure created by the hydrated alkali-silica gel leads to micro-crack formation within both the cement paste and aggregates. If left unchecked, ASR can cause extensive map-cracking, spalling of joints, excessive movements, and ultimately loss of service and safety of a structure.

Currently, the most popular method of preventing ASR related damage to concrete structures is the proper selection of aggregates. This can be achieved through field or laboratory performance assessments of a potential aggregate. Many various test methods have been developed to evaluate the potential of an aggregate to participate in expansive ASR. However, current test methods have limitations which have resulted in inaccurate results. Recognition of the unreliability of these testing methods have led to the need for occasional field assessments of the conditions of concrete structures to assure that no ASR gel formation has occurred, and where such ASR activity is discovered, the need for costly mitigation actions.

The present disclosure is directed to an improved test method for determining the likelihood of an aggregate, coarse or fine, or of a combination of aggregates within a proposed concrete mix of forming potentially dangerous expansive alkali-silica gels. Specifically, the present disclosure provides a chemical test methodology that evaluates the ASR reactivity of an aggregate, whether coarse or fine, as well as the ability to evaluate the ASR reactivity of a combination of coarse and fine aggregates within a proposed concrete job mix design by exposing the aggregate to simulated long-term pore solution conditions that it will experience in the field. The test methodology avoids the major limitations of the current testing standards—leaching and testing only individual aggregates—while providing an inexpensive, rapid, flexible test that does not require the preparation of concrete specimen or measuring the physical expansion of a test sample.

In a first preferred embodiment of the present disclosure a coarse aggregate is prepared for chemical reactive testing by crushing the coarse aggregate into two fractions—a finer fraction retained by a #100 sieve and a coarser fraction retained by a #50 sieve. The crushed aggregate is then washed with deionized water to remove any fine particles of aggregate that remain that would otherwise have passed through the two sieves. The remaining fractions are then fully dried. At least sixty grams of the crushed, washed and dried aggregate may be homogenized at a ratio of finer to coarser aggregate fractions of 1:1.66 for testing.

At least three replicates 10, each comprising a test tube or other acceptable container (as best seen in FIG. 1) made of a non-reactive material are prepared for each of four different test conditions—totaling twelve replicates 10. The plurality of replicates 10 for each test condition are prepared by adding a defined amount of calcium oxide (CaO) 14 to each replicate 10 as set forth in Table 1 below. The amount of CaO 14 varies depending on the test condition.

TABLE 1

| Test Condition | Calcium Oxide, g | Temperature, ° C. |
|---|---|---|
| 1 | 0.13 | 55 ± 2 |
| 2 | 0.25 | 55 ± 2 |
| 3 | 0.34 | 55 ± 2 |
| 4 | 0.25 | 80 ± 2 |

Each replicate then receives five grams of the homogenized aggregate 16 to be tested. At the preferred 1:1.66 ratio, that will be 3.125±0.005 g of the aggregate retained by the #50 sieve and 1.875±0.002 g of the aggregate retained by the #100 sieve. Finally, 25 mL of a soluble alkali 18, such as sodium hydroxide (NaOH) or potassium hydroxide (KOH) is added to each replicate 10. A 1 N solution of NaOH is preferred. Each replicate 10 is then securely sealed with a cap 12.

The plurality of replicates 10 representing the first three test conditions indicated in Table 1 are used to detect fast reacting aggregates and aggregates that react over a medium length of time. They are placed in an oven at 55°±2° C. as indicated in Table 1 for a period of 21 days. The plurality of replicates 10 representing the fourth test condition of Table 1 are used to detect slow reacting aggregates and are placed in a second oven at a temperature of 80°±2° C. for the same 21-day exposure period.

At the end of the 21-day exposure period, the contents of each replicate 10 are thoroughly mixed and individually vacuum filtered. The vacuum filtration should pass the mixed materials from the replicate 10 preferably through a glass microfiber filter having a pore size less than 0.7 μm. The filtrates from those individual replicates 10 exposed to the fourth test conditions of Table 1 are analyzed first. Where the average concentration of silicon of these individual fourth test condition filtrates is less than, or equal to 1 mM, the aggregate 16 is immediately classified as non-reactive (NR) and no further analysis of the remaining replicates 10 is required. Where the average concentration of silicon of these individual fourth test condition replicates 10 is greater than 1 mM, each of the filtrates from all the individual replicates 10 are individually analyzed for their concentrations of calcium, aluminum, and silicon. The reactivity index (RI) for each replicate 10 is calculated using the determined concentrations of calcium, aluminum, and silicon according to Equation 1.

Using multiple replicates 10 for each of the test conditions allows a tester to average the calculated RI for the aggregate under each test condition. The test provides for characterizing the reactivity of the tested aggregate, by comparing the calculated RI averages for all test conditions to a chart such as that shown in Table 2 below, which gives a general indication of the overall reactivity of the aggregate as one of five categories: non-mactive (NR), slow reactive (SR), moderately reactive (MR), highly reactive (HR), and very highly reactive (VIM).

TABLE 2

| Type of Aggregate | Condition 1 | Condition 2 | Condition 3 | Condition 4 | Aggregate Reactivity |
|---|---|---|---|---|---|
| Coarse | RI ≤ 0.45 for three conditions | | | RI ≤ 2 | NR |
| | 0.45 < RI ≤ 2 for one condition | | | 2 < RI ≤ 100 | SR |
| | 0.45 < RI ≤ 2 for at least two conditions | | | 2 < RI ≤ 100 | MR |
| | RI > 2 for at least one condition | | | 100 < RI ≤ 1000 | HR |
| | RI > 2 for at least one condition | | | RI > 1000 | VHR |
| Fine | RI ≤ 1 for three conditions | | | RI ≤ 10 | NR |
| | 1 < RI ≤ 10 for one condition | | | 10 < RI ≤ 150 | SR |
| | 1 < RI ≤ 10 for at least two conditions | | | 10 < RI ≤ 150 | MR |
| | RI > 10 for at least one condition | | | 150 < RI ≤ 1000 | HR |
| | RI > 10 for at least one condition | | | RI > 1000 | VHR |

In a second preferred embodiment of the present invention an accelerated chemical test methodology for determining the ASR reactivity of a fine aggregate is provided. As in the first preferred embodiment, at least three replicates 10 comprising a test tube or other acceptable container made of a non-reactive material are prepared for each of four different test conditions—totaling twelve replicates 10. The plurality of replicates 10 for each test condition are prepared by adding a defined amount of calcium oxide (CaO) 14 to each replicate 10 as set forth in Table 1.

Unlike with a coarse aggregate, crushing, sifting, and washing of the aggregate is not necessary. After inserting the prescribed amount of CaO 14 to the replicate 10, five grams of the fine aggregate 16 to be tested is added to each replicate 10, followed by 25 mL of a soluble alkali 18, preferably 1 N solution of NaOH. The replicates 10 are then sealed with a cap 12.

As in the first preferred embodiment, the plurality of replicates 10 representing the first three test conditions indicated in Table 1 are placed in an oven at 55°±2° C. as indicated in Table 1 for a period of 21 days. The plurality of replicates representing the fourth test condition of Table 1 are placed in a second oven at a temperature of 80°±2° C. for the same 21-day exposure period.

At the end of the 21-day exposure period, the contents of each replicate 10 are thoroughly mixed and individually vacuum filtered. The vacuum filtration should pass the mixed materials from the replicate 10 preferably through a glass microfiber filter having a pore size less than 0.7 μm. The filtrates from those individual replicates 10 exposed to the fourth test conditions of Table 1 are analyzed first. Where the average concentration of silicon of these individual fourth test condition filtrates is less than or equal to 1 mM, the aggregate 16 is immediately classified as non-reactive (NR) and no further analysis of the remaining replicates 10 is required. Where the average concentration of silicon of these individual fourth test condition replicates 10 is greater than 1 mM, each of the filtrates from all the individual replicates 10 are individually analyzed for their concentrations of calcium, aluminum, and silicon. As in the first preferred embodiment, the filtrate contents can be analyzed using inductively coupled plasma, atomic absorption, x-ray fluorescence, or other spectroscopic techniques. The reactivity index (RI) for each replicate 10 may then be calculated using Equation 1. The resultant averaged RIs for the test conditions for each test condition are then compared to the parameters set forth in Table 2 to determine the overall reactivity of the aggregate.

In a third preferred embodiment, an accelerated chemical test methodology is provided for testing a mixed aggregate in the same long-term pore conditions that it would experience during its proposed use. In order to simulate the composition of the pore solution—the alkalinity, ratio of fine to coarse aggregate, and calcium concentration—an analysis of the job mix report and the cement mill report are necessary to determine the correct amounts of fine and coarse aggregate 16, CaO 14, and a soluble alkali 18 to be included in a plurality of test replicates 10.

The amount of coarse aggregate remains five grams and is prepared as described above in the other preferred embodiments, including crushing, sifting and homogenizing at a ratio of 1:1.66 of fine crushed aggregate, that collected by a #100 sieve to coarse aggregate, that collected by the #50 sieve. The amount of fine aggregate to be included in each replicate 10 is based on the specified five-gram sample above and the aggregate mix called for in the job mix design. Similarly, the amount of CaO 14 per replicate 10 is calculated based on the alkali content and the specific amount of portlandite called for in the proposed job mix design, which is, in part, based on the cement mill report. The alkali concentration from the cement mill report is calculated assuming the full solubility of the alkali in the in the ordinary portland cement and the job mix design proportions. The Ca(OH)$_2$ content of a mix is determined based on the type of ordinary portland cement, the job mix design, and the measurement of Ca(OH)$_2$ content in the ordinary portland cement paste. The resulting value of Ca(OH)$_2$ is used to calculate the final amount of CaO 14 for use in each replicate 10.

The addition of a soluble alkali 18, such as sodium hydroxide (NaOH) or potassium hydroxide (KOH) to each replicate 10 is necessary to replicate the pH levels of the long-term pore solution, promote pozzolanic reaction, if any, in fine aggregates, and precipitation of different gel products, including ASR gels, within the system. Its inclusion further helps to preserve ionic strength, which along with pH, controls the hydroxide diffusivity in reactive aggregates.

As seen in FIG. 1, at least three test replicates 10 are prepared by adding the calculated amount of CaO 14, the calculated portion of fine aggregate and the two prepared fractions of the homogenized coarse aggregate (collectively 16), and 25 mL of a solution of soluble alkalis 18 at the predetermined concentration. As in other preferred embodiments, each of the test replicates 10, comprise a test tube or other acceptable container made of a non-reactive material. After completing the preparation of each replicate 10, it is sealed with a similarly non-reactive cap 12.

After their preparation and sealing, the at least three test replicates 10 in this preferred embodiment are placed in an oven at 55°±2° C. for a period of 21 days. Upon the completion of the exposure period, the solid portion remaining in each test replicate 10 is thoroughly mixed with the remaining liquid portions. The resulting suspension is filtered through a microfiber filter having a pore size of less than 0.7 μm.

The filtrates from each replicate is analyzed first for the concentration of silicon and the values from the three replicates is averaged. Where the average concentration of silicon of the filtrates is less than or equal to 1 mM, the aggregate 16 is immediately classified as non-reactive (NR) and no further analysis is required. Where the average concentration of silicon of the filtrates is greater than 1 mM, each of the filtrates are further analyzed for their concentrations of calcium and aluminum. Inductively coupled plasma, atomic absorption, x-ray fluorescence or other spectroscopy techniques, may be use to analyze these concentrations in the filtrates. A reactivity index (RI), a ratio of the concentration of silicon to that of aluminum and calcium combined, as indicated in Equation 1, is used to calculate the ASR reactivity of each individual replicate 10. The resulting RI values can be averaged to provide a more accurate predictor of the ASR reactivity of the mixed aggregate within the proposed job mix design.

The gel formed in the simulated pore solutions tested in the at least three replicates 10 characterized as having high concentrations of aluminum and calcium, and lower concentrations of silicon tend to lead to the formation of calcium-silica-hydrate gels. They will have a lower RI. Those formed in the simulated pore solutions and characterized as having lower concentrations of aluminum and calcium, and higher concentrations of silicon tend to lead to the formation of dangerously expansive ASR gels, and will have a higher RI. As such, an RI greater than 0.45 is indicative of the ASR reactivity of the test aggregate.

Although a detailed description of one preferred embodiment of the present disclosure has been expressed using specific terms and devices, such description is for illustrative purposes only. The words used are words of description rather than of limitation. It is understood that changes and variations may be made by those of ordinary skill in the art without departing from the spirit or scope of the present disclosure, which is set forth in the following claims. Additionally, it should be understood that aspects of various other embodiments may be interchanged either in whole or in part. Therefore, the spirit and scope of the appended claims should not be limited to the detailed description contained herein.

What is claimed is:

1. A chemical test method for assessing the likelihood of the formation of alkali-silica reaction gels in concrete comprising the steps of:

preparing a plurality of replicates for simulating a plurality of long-term pore conditions using a preselected aggregate;
heating a first portion of said plurality of replicates in a first oven for a period of time;
heating a second portion of said plurality of replicates in a second oven for said period of time;
filtering contents of each of said plurality of replicates after the expiry of said period of time;
measuring concentrations of silicon, aluminum, and calcium in each of said contents from said plurality of replicates; and
calculating a reactivity index value for said preselected aggregate in each of said plurality of replicates using said measured concentrations of silicon, aluminum, and calcium from each of said contents of each said plurality of replicates by dividing said measured concentration of silicon by a combined concentration of both said measured concentrations of aluminum and calcium, wherein said reactivity index value is indicative of an alkali-silica reactivity of said preselected aggregate in each of said plurality of simulated long-term pore conditions.

2. The method of claim 1, further comprising preparation of said preselected aggregate for testing where said preselected aggregate is coarse, including the steps of:
crushing said preselected aggregate;
sieving said crushed preselected aggregate and retaining those portions that are captured by #50 and #100 sieves;
washing and drying said retained crushed preselected aggregate portions separately; and
homogenizing said retained preselected aggregate portions by mixing them at a ratio of 1 part of said retained preselected aggregate portion captured by said #100 sieve to 1.66 parts of said retained preselected aggregate portion captured by said #50 sieve.

3. The method of claim 1, wherein the preparation of each of said plurality of replicates further comprises:
selecting a non-reactive container;
adding a defined amount of calcium oxide to said container;
adding five grams of said preselected aggregate to said container;
adding a defined amount of a soluble alkali to said container; and
sealing said container.

4. The method of claim 3, wherein said defined amount of calcium oxide is determined based on a pre-established testing chart; and
wherein said pre-established testing chart provides at least four different calcium oxide amounts, one each for each of at least four simulated long-term pore conditions.

5. The method of claim 4, wherein said defined amount of said soluble alkali is 25 mL of 1 N sodium hydroxide.

6. The method of claim 5, wherein at least three replicates are prepared for each of said at least four simulated long-term pore conditions; and
wherein said calculated reactivity index value for each of said simulated long-term pore conditions under test is an average of said calculated reactivity index values for each of said at least three replicates for each of said at least four simulated long-term pore conditions.

7. The method of claim 6, wherein said calculated reactivity index value for each of said at least four simulated long-term pore conditions are compared to a pre-established chart to determine the likelihood of the formation of alkali-silica reaction gels in concrete for said preselected aggregate.

8. The method of claim 1, wherein said first portion of said plurality of replicates are heated in said first oven at 55°±2° C.

9. The method of claim 1, wherein said second portion of said plurality of replicates are heated in said second oven at 80°±2° C.

10. The method of claim 1, wherein said period of time said first and second portions of said plurality of replicates are heated in said first and second ovens is twenty-one days.

11. The method of claim 1, wherein said filtering of said contents of each replicate is performed via vacuum filtration through a glass microfiber filter having a pore size smaller than 0.7 μm.

12. A chemical test method for assessing the likelihood of the formation of alkali-silica reaction gels in a defined concrete job mix comprising the steps of:
preparing a mixed aggregate for testing;
preparing at least three replicates for simulating long-term pore conditions of said defined concrete job mix using said mixed aggregate;
heating said at least three replicates in an oven for a period of time;
filtering contents of each of said at least three replicates after the expiry of said period of time;
measuring concentrations of silicon, aluminum, and calcium in each of said contents from said at least three replicates; and
calculating a reactivity index value using said measured concentrations of silicon, aluminum, and calcium from each of said contents of each said at least three replicates by dividing said measured concentration of silicon by a combined concentration of both said measured concentrations of aluminum and calcium, wherein said reactivity index value is indicative of an alkali-silica reactivity of said mixed aggregate in said defined concrete job mix and the likelihood of the formation of alkali-silica reaction gels in said defined concrete job mix using said mixed aggregate.

13. The method of claim 12, wherein said preparation of said mixed aggregate further comprises the steps of:
crushing a coarse portion of said mixed aggregate;
sifting said crushed aggregate and retaining those portions that are captured by #50 and #100 sieves;
washing and drying said retained crushed aggregate portions separately; and
homogenizing said retained aggregate portions by mixing them at a ratio of 1 part of said retained aggregate portion captured by said #100 sieve to 1.66 parts of said retained aggregate portion captured by said #50 sieve.

14. The method of claim 13, wherein the preparation of each of said at least three replicates further comprises:
selecting non-reactive container;
adding a calculated amount of calcium oxide to said container;
adding an amount of fine aggregate to said container as required to satisfy said defined concrete job mix based on five grams of homogenized coarse aggregate;
adding said five grams of said homogenized coarse aggregate to said container;
adding a defined amount of a soluble alkali to said container; and
sealing said container.

15. The method of claim 14, wherein said amount of calcium oxide is calculated based on said concrete job mix, a cement mill report, and a calculated amount of calcium hydroxide in an ordinary Portland cement paste in a cement mix called for in said cement mill report.

16. The method of claim 15, wherein said defined amount of said soluble alkali is 25 mL of a solution containing alkali concentration of sodium hydroxide and potassium hydroxide corresponding to an alkali content specified in said cement mill report.

17. The method of claim 12, wherein said at least three replicates are heated in said oven at 55° C. for twenty-one days.

18. The method of claim 12, wherein said filtering of said contents of each replicate is performed via vacuum filtration through a glass microfiber filter having a pore size smaller than 0.7 μm.

19. A method for assessing the likelihood of the formation of alkali-silica reaction gels in concrete comprising the steps of:
 preparing a plurality of replicates for simulating long-term pore conditions of a proposed concrete mix using a specified aggregate by adding a predetermined amount of calcium oxide, a predetermined amount of said specified aggregate and a soluble alkali to a container to form each of said plurality of replicates;
 conducting an accelerated exposure of said plurality of replicates to simulated long-term pore conditions by heating said plurality of replicates in an oven for a predefined period of time at a predefined temperature;
 analyzing contents of each of said plurality of replicates for concentrations of silicon, aluminum, and calcium after said predefined period of time; and
 calculating a reactivity index value for each of said plurality of replicates by dividing a measured concentration of silicon by a measured combined concentration of both said aluminum and calcium in each of said plurality of replicates and averaging their values to obtain an average calculated reactivity index value;
 wherein an average calculated reactivity index value greater than 0.45 is indicative of the likely formation of alkali-silica reaction gels in said proposed concrete mix using said specified aggregate.

* * * * *